United States Patent [19]

Semkina et al.

[11] 3,937,670

[45] Feb. 10, 1976

[54] COMPOSITION FOR PREPARING SOLID ELECTROLYTES AND THE FORMULATION OF A SOLID ELECTROLYTE

[76] Inventors: Novella Vladimirovna Semkina, prospekt Bljukhera, 71/1, kv. 38; Zinaida Ulyanovna Evdokimova, pereulok Vstrechny, 7, korpus 1, kv. 7; Konstantin Sergeevich Assanovich, 4 ulitsa Cheljuskintsev, 18, kv. 84, all of Sverdlovsk; Anatoly Alexandrovich Rozlovsky, ulitsa 3 Olovozavodskaya 3, kv. 10, Novosibirsk, all of U.S.S.R.

[22] Filed: Oct. 2, 1973

[21] Appl. No.: 402,814

[52] U.S. Cl. ............... 252/519; 106/65; 252/518; 252/520
[51] Int. Cl.² ............................................ H01B 1/08
[58] Field of Search .......... 252/518, 519, 520, 62.2; 106/65; 136/86 F, 153

[56] References Cited
UNITED STATES PATENTS
3,436,269   4/1969   Mitoff............................. 252/519 X

*Primary Examiner*—Leland A. Sebastian
*Assistant Examiner*—E. Suzanne Parr
*Attorney, Agent, or Firm*—Holman & Stern

[57] ABSTRACT

Proposed herein is a compound for making solid electrolytes, comprising alumina as a base and additives of titania, iron oxide or zinc oxide.

Likewise proposed herein is a solid electrolyte prepared from said composition and having the following formulation (in percent by weight):

| | |
|---|---|
| alumina | 92 to 98 |
| titania | 0.5 to 2 |
| zinc oxide or iron oxide | 0.5 to 5.0 |
| and other admixtures | up to 1 |

An advantageous feature of the compound and of electrolytes made therefrom resides in the fact that the cationic conductance therein is substituted for ionic conductance which renders such solid electrolytes suitable for detecting metallic admixtures in various metals by the e.m.f. determining method.

Said method proves advantageous due to the fact that it may be rapidly carried out. Besides, it enables a continuous monitoring of the metal composition in the course of its melting process and thereby provides for the possibility of bringing automation into the melting process.

2 Claims, No Drawings

COMPOSITION FOR PREPARING SOLID ELECTROLYTES AND THE FORMULATION OF A SOLID ELECTROLYTE

This invention relates generally to metallurgical industry and more specifically to compounds for preparing solid electrolytes used in the detection of the admixtures in metals.

The invention particularly relates to those compounds which are suitable in the preparation of solid electrolytes useful in the detection of metallic admixtures in various metals.

One known prior art compound which has been used extensively for making solid electrolytes, comprises (in weight percent): zirconia, 94; and calcium oxide, 6. Solid electrolytes made of such a compound have the following weight percentage composition: zirconia, 94; and calcium oxide, 6.

It is also known that attempts have been made to make solid electrolytes from magnesia, silica or from mullite.

Apart from the above, the USSR has recently developed the compounds having the character set forth hereinbefore, yet having the following composition (in weight percent):

alumina from 85 to 95
zirconia from 4 to 10
titania from 1 to 5.

The solid electrolytes prepared from such compounds have the following weight percentage composition:

alumina — 84 to 94
zirconia — 4 to 10
titania — 1 to 5

, and admixtures of alkali-metal oxides, magnesia and calcium oxide — up to 1.

All the afore-discussed compounds are intended for making such solid electrolytes therefrom which are suitable only for detecting an admixture of free oxygen in steels, and which being incapable of detecting metallic admixtures therein.

Metallic admixtures in various metals have so far been detected by the method of chemical or spectral analysis.

It is common knowledge that said methods are applicable under laboratory conditions only, which take much time to perform and, consequently, are of low efficiency and, moreover, fail to effect an automated complex monitoring of the metal composition during its melting process.

It is an essential object of the present invention to provide such a compound that would enable the preparation of electrolytes suitable for detecting metallic admixtures in a metal.

It is another object of the present invention to provide such electrolytes that would enable the use of a more efficient method in detecting metallic admixtures, viz., the method based upon determining the e.m.f.

It is still another equally important object of the present invention to ensure a continuous automatic monitoring of the metal composition in the course of the melting process thereof.

Said objects are achieved in a compound based upon sintered alumina with a titania additive and adapted for making a solid electrolyte therefrom, containing, according to the invention also an additive of zinc oxide or iron oxide.

Specifically, the compound of the invention contains from 0.5 to 5 percent of the iron oxide or zinc oxide and from 0.5 to 2 percent of titania of the total weight of the compound.

Accordingly, the solid electrolyte prepared from said compound has the following weight percentage composition:
alumina — 92 to 98
titania — 0.5 to 2
zinc oxide or iron oxide — 0.5 to 5.0
other admixtures — up to 1

Such a compound and the respective solid electrolyte produced therefrom enable the cationic conductance to be obtained and thereby make it possible to provide a method of detecting metallic admixtures.

Specified below is a detailed disclosure of the invention given by way of specific illustrative examples of the formulation of the compounds and respective solid electrolytes made from said compounds.

According to the invention, the composition contains (in percent by weight):

| | |
|---|---|
| alumina | 93 to 99.5 |
| zinc oxide or iron oxide | 0.5 to 5.0 |
| titania | 0.5 to 2.0 |

The addition of either zinc oxide or iron oxide depends upon whether the admixture of the former or of the latter has to be detected with the use of an electrolyte made of said compound. It is thus reasonable that a zinc-oxide additive should be used for the detection of a zinc-oxide admixture in a metal and an iron-oxide additive in the case of an iron-oxide admixture in a metal.

For the preparation of the herein-proposed compound use is made of commercial alumina having been sintered at from 1450° to 1500°C beforehand, such temperatures being those commonly used in alumina-sintering. The sintered alumina is then subjected to grinding in a vibration mill or in any other arrangement suitable for that purpose, until the size of particles of the main fraction is not over from 2 to 3 microns.

While being ground, alumina is doped with one of the aforesaid additives, viz. iron oxide or zinc oxide, as well as titania.

As a result of such a combined grinding, the powderlike compound is obtained which serves as the material for preparing the solid electrolytes.

The preparation is carried out according to the known technique which will hereinafter be disclosed in detail.

Paraffin is introduced into the bulk of the powderlike compound prepared as described herein above and which being taken in an amount of from 14 to 16 percent of the weight of the powderlike compound, and the mixture is stirred while heating up to 60°C. Then the resultant compound is used for making, by the drawing method, the tubes with one closed end. The thus-drawn tubes are heated to 220°C to eliminate from 67 to 80 percent of paraffin therefrom. Next the tubes are sintered at 1550° to 1600°C.

The thus-obtained sintered solid electrolytes have, according to the original compound they are made from, the following weight percentage composition:

| | |
|---|---|
| alumina | 92 to 98 |
| titania | 0.5 to 2.0 |
| zinc oxide or iron oxide | 0.5 to 5.0 | with other admixtures being the balance.

Such solid electrolytes are used for detecting metallic admixtures, largely zinc oxide or iron oxide, in various metals, mostly non-ferrous metals.

Specifically, the solid electrolytes containing zinc oxide as an additive, are intended mostly for detecting zinc admixtures in a metal, whereas those containing iron oxide as an additive, are mostly for detecting iron admixtures therein. Said admixtures can be detected in any metal, which is usually done during the course of its melting process.

Given below are a number of exemplary formulations of the compound and the respective solid electrolytes made therefrom.

EXAMPLE 1

The weight percent of the composition is:
alumina 98.5
titania 0.6
zinc oxide 0.9.
, and the weight percent of the solid electrolyte composition is:
alumina 97.5
titania 0.6
zinc oxide 0.9
admixtures of oxides of alkali metals, calcium oxide and magnesia -1%

The electrolyte features the following properties:
open-pore percentage, 0.40
apparent density, 3.89 g/cm³
exhibits a thermal stability within a temperature range of from 1300° to 20°C (air), and 6 heat cycles cationic conductance, 100 percent.

EXAMPLE 2

The weight percent of the composition is:
alumina 95.5
titania 1.5
zinc oxide 3.0
, and the weight percent of the solid electrolyte composition is:
alumina 94.5
titania 1.5
zinc oxide 3.0
admixtures of oxides of alkali metals, calcium oxide and magnesia 1%.

The properties of the solid electrolyte are:
open-pore percentage, 2.0
apparent density, 3.73 g/cm³
exhibits thermal stability within temperatures ranging from 1300° to 20°C (air), and the 6 heat cycles cationic conductance, 100 percent.

EXAMPLE 3

The weight percent of the composition is:
alumina 92.8
titania 2.2
zinc oxide 5
, and the weight percentage composition of the solid electrolyte:
alumina 91.8
titania 2.2
zinc oxide 5
, and the admixtures of oxides of alkali metals, magnesia and calcium oxide 1.

The properties of the solid electrolyte are:
open-pore percentage, 1.9
apparent density, 3.70 g/cm³
exhibits thermal stability within temperatures ranging from 1300° to 20°C (air), and the 7 heat cycles cationic conductance, 100 percent.

EXAMPLE 4

The weight percent of the composition is:
alumina 98.3
titania 0.6
iron oxide 1.1
The weight percentage composition of the solid electrolyte:
alumina 97.3
titania 0.6
iron oxide 1.1
, and the admixtures of oxides of alkali metals, magnesia and calcium oxide 1.1

The properties of the solid electrolyte are:
open-pore percentage, 0.75
apparent density, 3.81 g/cm³
exhibits thermal stability within temperatures ranging from 1300 to 20°C (air), and the 10 heat cycles cationic conductance, 100 percent.

EXAMPLE 5

The weight percent of the composition is:
alumina 95.5
titania 1.5
iron oxide 3
The weight percentage composition of the solid electrolyte:
alumina 94.5
titania 1.5
iron oxide 3
, and the admixtures of oxides of alkali metals, magnesia and calcium oxide 1

The properties of the solid electrolyte are:
open-pore percentage, 1.00
apparent density, 3.85 g/cm³,
exhibits thermal stability within temperatures ranging from 1300 to 20°C (air, and the 8 heat cycles cationic conductance, 100 percent.

EXAMPLE 6

The weight percent of the composition is:
alumina 92.8
titania 2.2
iron oxide 5
, the weight percentage composition of the solid electrolyte:
alumina 91.8
titania 2.2
iron oxide 5
, and the admixtures of oxides of alkali metals, magnesia and calcium oxide 1.

The properties of the solid electrolyte are:

open-pore percentage, 1.8
apparent density, 3.89 g/cm³
exhibits thermal stability within temperatures ranging from 1300 to 20°C (air), and the 7 heat cycles cationic conductance, 100 percent.

The tube manufacturing technique is the same for all six examples stated hereinbefore.

The method of detecting the metallic admixtures with the use of the afore-described solid electrolytes is not described in the present disclosure as the e.m.f. method for same is known heretofore and is readily available from the literature and, also, it may be the subject of another invention.

What is claimed is:

1. A composition for preparing solid electrolytes, consisting essentially of in percent by weight, sintered alumina, 93 to 99.5; a substance selected from the group consisting of zinc oxide and iron oxide, 0.5 to 5.0; and titania, 0.5 to 2.0 of the total weight of the composition.

2. A solid electrolyte prepared from a composition consisting of alumina and additives of titania and a substance selected from the group consisting of zinc oxide and iron oxide, said electrolyte having the following weight percentage composition:

alumina — 92 to 98 wt.%
titania — 0.5 to 2.0 wt.%,
the substance selected from the group consisting of zinc oxide and iron oxide — 0.5 to 5.0 wt.%, and other admixtures, comprising alkali metal oxides, magnesia, and calcium oxide, up to 1%.

* * * * *